United States Patent [19]
Hirabayashi et al.

[11] 4,451,561
[45] May 29, 1984

[54] HEAT-DEVELOPMENT-TYPE IMAGE RECORDING MATERIAL

[75] Inventors: Shigeto Hirabayashi, Hachioji; Toyoaki Masukawa, Hinode; Wataru Ishikawa, Hachioji; Tetsuya Harada, Chofu, all of Japan

[73] Assignee: Konishiroku Photo Industry Co., Ltd., Japan

[21] Appl. No.: 487,729

[22] Filed: Apr. 22, 1983

[30] Foreign Application Priority Data

Apr. 28, 1982 [JP] Japan ................................ 57-73215

[51] Int. Cl.³ .............................................. G03C 1/02
[52] U.S. Cl. .................................... 430/619; 430/353; 430/611; 430/614; 430/620
[58] Field of Search ............... 430/619, 620, 353, 611, 430/614, 600, 603, 487

[56] References Cited

U.S. PATENT DOCUMENTS

| | | | |
|---|---|---|---|
| 3,330,663 | 7/1967 | Weyde et al. | 430/620 |
| 3,832,186 | 8/1974 | Masuda et al. | 430/619 |
| 3,881,938 | 5/1975 | Masuda et al. | 430/619 |
| 4,144,072 | 3/1979 | Ikenoue et al. | 430/353 |
| 4,170,480 | 10/1979 | Ikenoue et al. | 430/619 |
| 4,245,033 | 1/1981 | Eida et al. | 430/620 |

Primary Examiner—J. Travis Brown
Attorney, Agent, or Firm—Finnegan, Henderson, Farabow, Garrett & Dunner

[57] ABSTRACT

A heat-development-type image recording material comprising an organic silver salt, a reducing agent, a binder, and an amido derivative of a 5-mercapto-1,2,4-triazole or a 5-mercapto-1,3,4-thiadiazole.

10 Claims, No Drawings

HEAT-DEVELOPMENT-TYPE IMAGE RECORDING MATERIAL

BACKGROUND OF THE INVENTION

The present invention relates to a heat-development-type image recording material, and more particularly to a heat-development-type image recording material whose developability is markedly improved.

The heat-development-type image recording material herein means those recording materials capable of producing an image through the amplification by the heat development of a latent image formed by certain means. To be more concrete, these materials may be broadly classified according to means for the formation of a latent image as heat-development-type light-sensitive materials comprising a silver halide which is exposed to light to thereby form a latent image and electro-thermo recording magerials which produce a latent image by the injection of electric charge.

As for the aforesaid heat-development-type light-sensitive material, for example, Japanese Patent Examined Publication Nos. 4921/1968 and 4924/1968 disclose those light-sensitive materials comprising an organic silver salt, silver halide and reducing agent. These heat-development-type light-sensitive materials are such that the silver halide is exposed to light to thereby form a latent image which serves as a catalyst nucleus for the oxidation-reduction reaction by heating of the organic silver salt with the reducing agent; namely a silver image is obtained by the so-called dry physical development process.

As to the aforesaid heat-development-type electro-thermo recording material, Japanese Patent Publication Open to Public Inspection (hereinafter referred to as Japanese Patent O.P.I. Publication) No. 63621/1976, 23635/1978, 133041/1978, 144752/1978, 101333/1979 and 106229/1979 disclose those electro-thermo recording materials comprising an organic silver salt and reducing agent.

Generally speaking, although those image forming compositions used in these heat-development-type image recording materials are comprised basically of an organic silver salt and reducing agent, it is known that a development accelerator and toning agent are further added to the image composition for the purpose of obtaining a higher maximum density and a more satisfactorily toned image.

The development accelerator and toning agent include, e.g., those derivatives of phthalimide, pyrazolone, quinazolinone, N-hydroxynaphthalimide, benzoxazine, naphthoxazinedione, 2,3-dihydro-phthalazinedione, 2,3-dihydro-1,3-oxazine-2,4-dione, oxypyridine, aminopyridine, hydroxyquinoline, aminoquinoline, isocarbostyryl, sulfonamide, 2H-1,3-benzothiazine-2,4-(3H)dione, benzotriazine, mercaptotriazole, dimercaptotetrazapentalene, phthalic acid, phthalazine, naphthalic acid, phthalamic acid, phthalazinone, and the like, as described in Japanese Patent O.P.I. Publication Nos. 4928/1971, 6077/1971, 5019/1974, 5020/1974, 91215/1974, 107727/1974, 2524/1975, 67132/1975, 67641/1975, 114217/1975, 33722/1977, 99813/1977, 1020/1978, 55115/1978, 76020/1978, 125014/1978, 156523/1979, 156524/1979, 156525/1979, 156526/1979, 4060/19780, 4061/1980, 32015/1980, and the like, West German Pat. Nos. 2,140,406, 2,147,063 and 2,220,618, and U.S. Pat. Nos. 3,080,254, 3,847,612, 3,782,941, 3,994,732, 4,132,282 and 4,201,582. However, many of these compounds, although effectively usable as development accelerators, increase fog or adversely affect the preservability of undeveloped or developed heat-development-type image recording materials, and thus any compounds as such agents having sufficient desired characteristics have still not been found.

BRIEF SUMMARY OF THE INVENTION

It is an object of the present invention to provide a heat-development-type image recording material having a good developability and high maximum density and producing little fog.

It is another object of the present invention to provide a heat-development-type image recording material having an excellent preservability in both the undeveloped and developed conditions thereof.

The above-described objects of this invention are accomplished by a heat-development-type image recording material comprising on a support a heat-development-type image recording layer containing
  (a) an organic silver salt,
  (b) a reducing agent,
  (c) a binder, and
  (d) at least one compound of following formula [I]:

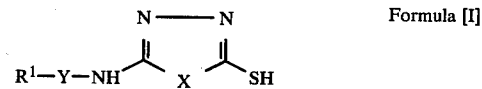

Formula [I]

wherein $R^1$ represents a hydrogen atom, a hydroxy radical or a substituted or unsubstituted alkyl, alkenyl, aryl or alkoxy radical; Y represents a sulfonyl or a carbonyl radical; and X represents a sulfur atom or $=N-R^2$ wherein $R^2$ is a hydrogen atom, an amino radical or a substituted or unsubstituted alkyl, aryl or alkenyl radical.

PREFERRED EMBODIMENT

The heat-development-type image recording material of the present invention will further be described in detail below:

The (a) organic silver salt to be contained in a heat-development-type image recording layer of the heat-development-type image recording material of this invention includes silver salts of aliphatic carboxylic acids such as, e.g., silver laurate, silver myristate, silver palmitate, silver stearate, silver arachidonate, silver behenate, silver γ-(1-phenyltetrazolethio)acetate, and the like; silver salts of aromatic carboxylic acids such as, e.g., silver benzoate, silver phthalate, and the like; silver salts of imino radical-having organic compounds such as, e.g., silver salts of benzotriazoles, silver salt of saccharin, silver salt of phthalazinone, silver salt of phthalimide, and the like; silver salts of mercapto radical- or thione radical-having compounds such as, e.g., silver salt of 2-mercaptobenzoxazole, silver salt of mercaptoxadiazole, silver salt of 2-mercaptobenzothiazole, silver salt of 2-mercaptobenzoimidazole, silver salt of 3-mercapto-4-phenyl-1,2,4-triazole, and further silver salt of 4-hydroxy-6-methyl-1,3,3a,7-tetraazaindene, silver salt of 5-methyl-7-hydroxy-1,2,3,4,6-pentazaindene, and the like, as described in, e.g., Japanese Patent Examined Publication Nos. 4921/1968, 26582/1969, 18416/1970, 12700/1970 and 22185/1970, Japanese Patent O.P.I. Publication Nos. 52626/1974, 31728/1977, 137321/1977, 141222/1977, 36224/1978 and 37610/1978, and U.S. Pat. Nos. 3,330,633, 3,794,496, 4,105,451, 4,123,274 and 4,168,980, and the like.

In the present invention, preferred among the above organic silver salts are the silver salts of the imino radical-having organic compounds and particularly the silver salts of benzotriazoles are most preferred.

Examples of the silver salts of benzotriazoles are, for example, silver salt of benzotriazole, silver salt of 5-chlorobenzotriazole, silver salt of 5-methylbenzotriazole, silver salt of 5-aminobenzotriazole, silver salt of 5-methoxybenzotriazole, silver salt of 4-nitrobenzotriazole, silver salt of 5-nitrobenzotriazole, silver salt of 5-nitro-6-chlorobenzotriazole, silver salt of 5-nitro-6-methylbenzotriazole, silver salt of 5-nitro-6-methoxybenzotriazole, silver salt of 5-nitro-7-phenylbenzotriazole, silver salt of 4-hydroxy-5-nitrobenaotriazole, silver salt of 4-hydroxy-7-nitrobenzotriazole, silver salt of 4-hydroxy-5,7-dinitrobenzotriazole, silver salt of 4-hydroxy-5-nitro-6-chlorobenzotriazole, silver salt of 4-hydroxy-5-nitro-6-methylbenzotriazole, silver salt of 4-sulfo-6-nitrobenzotriazole, silver salt of 4-carboxy-6-nitrobenzotriazole, silver salt of 5-carboxy-6-nitrobenzotriazole, silver salt of 4-carbamoyl-6-nitrobenzotriazole, silver salt of 4-sulfamoyl-6-nitrobenzotriazole, silver salt of 5-carboxymethyl-6-nitrobenzotriazole, silver salt of 5-hydroxycarbonylmethoxy-6-nitrobenzotriazole, silver salt of 5-nitro-7-cyanobenzotriazole, silver salt of 5-amino-6-nitrobenzotriazole, silver salt of 5-nitro-7-(p-nitrophenyl)benzotriazole, silver salt of 5,7-dinitro-6-methylbenzotriazole, silver salt of 5,7-dinitro-6-chlorobenzotriazole, silver salt of 5,7-dinitro-6-methoxybenzotriazole, silver salt of 4-hydroxybenzotriazole, silver salt of 5-hydroxybenzotriazole, silver salt of 4-sulfobenzotriazole, silver salt of 5-sulfobenzotriazole, silver salt of benzotriazole-4-sodium sulfonate, silver salt of benzotriazole-5-sodium sulfonate, silver salt of benzotriazole-4-potassium sulfonate, silver salt of benzotriazole-5-potassium sulfonate, silver salt of benzotriazole-4-ammonium sulfonate, silver salt of benzotriazole-5-ammonium sulfonate, silver salt of carboxybenzotriazole, silver salt of 5-carboxybenzotriazole, silver salt of benzotriazole-4-sodium carboxylate, silver salt of benzotriazole-5-sodium carboxylate, silver salt of benzotriazole-4-potassium carboxylate, silver salt of benzotriazole-5-potassium carboxylate, silver salt of benzotriazole-4-ammonium carboxylate, silver salt of benzotriazole-5-ammonium carboxylate, silver salt of carbamoylbenzotriazole, silver salt of 4-sulfamoylbenzotriazole, silver salt of 5-carboxy-6-hydroxybenzotriazole, silver salt of 5-carboxy-7-sulfobenzotriazole, silver salt of 4-hydroxy-5-sulfobenzotriazole, silver salt of hydroxy-7-sulfobenzotriazole, silver salt of 5,6-dicarboxybenzotriazole, silver salt of 4,6-dihydroxybenzotriazole, silver salt of 4-hydroxy-5-chlorobenzotriazole, silver salt of 4-hydroxy-5-methylbenzotriazole, silver salt of 4-hydroxy-5-methoxybenzotriazole, silver salt of 4-hydroxy-5-nitrobenzotriazole, silver salt of 4-hydroxy-5-cyanobenzotriazole, silver salt of 4-hydroxy-5-aminobenzotriazole, silver salt of hydroxy-5-acetamidobenzotriazole, silver salt of 4-hydroxy-5-benzenesulfonamidobenzotriazole, silver salt of 4-hydroxy-5-hydroxycarbonylmethoxybenzotriazole, silver salt of 4-hydroxy-5-ethoxycarbonylmethoxybenzotriazole, silver salt of 4-hydroxy-5-carboxymethylbenzotriazole, silver salt of 4-hydroxy-5-ethoxycarbonylmethylbenzotriazole, silver salt of 4-hydroxy-5-phenylbenzotriazole, silver salt of 4-hydroxy-5-(p-nitrophenyl)benzotriazole, silver salt of 4-hydroxy-5-(p-sulfophenyl)benzotriazole, silver salt of 4-sulfo-5-chlorobenzotriazole, silver salt of 4-sulfo-5-methylbenzotriazole, silver salt of 4-sulfo-5-methoxybenzotriazole, silver salt of 4-sulfo-5-cyanobenzotriazole, silver salt of 4-sulfo-5-aminobenzotriazole, silver salt of 4-sulfo-5-acetamidobenzotriazole, silver salt of 4-sulfo-5-benzenesulfonamidobenzotriazole, silver salt of 4-sulfo-5-hydroxycarbonylmethoxybenzotriazole, silver salt of 4-sulfo-5-ethoxycarbonylmethoxybenzotriazole, silver salt of 4-hydroxy-5-carboxybenzotriazole, silver salt of 4-sulfo-5-carboxymethylbenzotriazole, silver salt of 4-sulfo-5-ethoxycarbonylmethylbenzotriazole, silver salt of 4-sulfo-5-phenylbenzotriazole, silver salt of 4-sulfo-5-(p-nitrophenyl)benzotriazole, silver salt of 4-sulfo-5-(p-sulfophenyl)benzotriazole, silver salt of 4-sulfo-5-methoxy-6-chlorobenzotriazole, silver salt of 4-sulfo-5-chloro-6-carboxybenzotriazole, silver salt of 4-carboxy-5-chlorobenzotriazole, silver salt of 4-carboxy-5-methylbenzotriazole, silver salt of 4-carboxy-5-nitrobenzotriazole, silver salt of 4-carboxy-5-aminobenzotriazole, silver salt of 4-carboxy-5-methoxybenzotriazole, silver salt of 4-carboxy-5-acetamidobenzotriazole, silver salt of 4-carboxy-5-ethoxycarbonylmethoxybenzotriazole, silver salt of 4-carboxy-5-carboxymethylbenzotriazole, silver salt of 4-carboxy-5-phenylbenzotriazole, silver salt of 4-carboxy-5-(p-nitrophenyl)benzotriazole, silver salt of 4-carboxy-5-methyl-7-sulfobenzotriazole, and the like. These compounds may be used singly or in combination of two or more kinds.

The heat-development-type image recording layer of the heat-development-type image recording material of the present invention may be provided in the form of either a single layer or a plurality of layers, and any of the above organic silver salts may be used in a quantity of from 0.5 to 50 mg and more preferably from 1 to 20 mg in silver equivalent per $dm^2$ of each layer.

When providing a heat-development-type image recording layer in the form of a plurality of layers, the tone of an image to be produced, the foot and shoulder of the density curve of the image, or the inclination of the overall density curve may be controlled by varying the kinds and the containing quantities of the aforementioned organic silver salt and a reducing agent which will be mentioned hereinafter to be incorporated together in each same layer. Alternatively, the salt and agent may be incorporated separately into separate layers to increase the stability of the recording material. In this case, a compound having Formula [I] is desirable to be incorporated in the layer containing silver salt of a benzotriazole.

Further, the (b) reducing agent to be contained in the heat-development-type image recording layer of the present invention includes phenols such as, e.g., p-phenylphenol, p-methoxyphenol, 2,6-di-tert-butyl-p-cresol, N-methyl-p-aminophenol, and the like; sulfonamidophenols such as, e.g., 4-benzenesulfonamidophenol, 2-benzenesulfonamidophenol, 2,6-dichloro-4-benzenesulfonamidophenol, 2,6-dibromo-4-(p-toluenesufonamide)phenol, and the like; di- or polyhydroxybenzenes such as, e.g., hydroquinone, tert-butylhydroquinone, 2,6-dimethylhydroquinone, chlorohydroquinone, carboxyhydroquinone, catechol, 3-carboxycatechol, and the like; naphthols such as, e.g., α-naphthol, β-naphthol, 4-aminonaphthol, 4-methoxynaphthol, and the like; hydroxybinaphthyls and methylene-binaphthols such as, e.g., 1,1'-dihydroxy-2,2'-binaphthyl, 6,6'-dibromo-2,2'-dihydroxy-1,1'-binaphthyl, 6,6'-dinitro-2,2'-dihydroxy-1,1'-binaphthyl, 4,4'-dimethoxy-1,1'-dihydroxy-2,2'-binaphthyl, bis(2-hydroxy-1-naphthyl)methane, and the like; methylene-bisphenols such as 1,1-bis(2-hydroxy-3,5-dimethylphenyl)3,5,5-trimethylhexane, 1,1-bis(2-hydroxy-3-tert-butyl-5-methylphenyl)methane, 1,1-bis(2-hydroxy-3,5-di-tert-butylphenyl) methane, 2,6-methylene-bis(2-hydroxy-3-tert-butyl-5-methylphenyl)-4-methylphenol, α-phenyl-α,α-bis(2-hydroxy-3,5-di-tert-butyl-phenyl)methane, α-phenyl-α,αbis(2-hydroxy-3-tert-butyl-5-methylphenyl)methane, 1,1-bis(2-hydroxy-3,5-dimethylphenyl)-2-methylpropane, 1,1,5,5-tetrakis(2-hydroxy-3,5-dimethylphenyl)-2,4-ethylpentane, 2,2-bis(4-hydroxy-3,5-dimethylphenyl)propane, 2,2-bis(4-hydroxy-3-methyl-5-tert-butylphenyl)propane, 2,2-bis(4-hydroxy-3,5-di-tert-butylphenyl)propane, and the like; ascorbic acids, 3-pyrazolidones, pyrazolines, pyrazolones, hydrozones, and paraphenylenediamines.

In the case of using hydrazones and para-phenylenediamines as reducing agents, a color image can be obtained by the use of such agents together with a phenol-type or a naphthol-type compound and an active methylene-having compound such as pyrazolone, pyrazolotriazole, indazole, pyrazolobenzimidazole, pyrazoline, or the like, such as desicribed in U.S. Pat. Nos. 3,531,286 and 3,764,328, and Japanese Patent O.P.I. Publication No. 27132/1981.

The foregoing reducing agents may be used singly or in combination of two or more kinds. The using quantity of such reducing agents, although different according to the kind of the organic silver salt used and the kind of other additives used, is normally from 0.05 to 10 moles and preferably from 0.1 to 3 moles per mole of the organic silver salt used.

The heat-development-type image recording material of the present invention may, if necessary, contain a light-sensitive silver halide in addition to aforesaid various compounds. Those light-sensitive silver halide applicable to the recording material include silver chloride, silver bromide, silver iodide, silver chlorobromide, silver chloroiodide, silver iodobromide, silver chlorobromoiodide, and the like. Any of these light-sensitive silver halides may be prepared by any arbitrary method such as the single jet method, double jet method, etc., which are known to those skilled in the photographic art, but particularly in the present invention, desirable results are given by a light-sensitive silver halide emulsion that is prepared in accordance with ordinary procedures for the preparation of a gelatino-silver halide emulsion of photographic material.

The light-sensitive silver halide emulsion may be chemically sensitized by any arbitrary method known in the photographic technological field. Such sensitization methods include the gold sensitization method, sulfur sensitization method, gold-sulfur sensitization method, reduction sensitization method, and the like.

The silver halide in the above light-sensitive silver halide emulison may be either coarse-grained or fine-grained, but the preferred particle size thereof is from about 1.5 to about 0.001 micron and more preferably from about 0.5 to about 0.05 micron.

The light-sensitive silver halide emulsion prepared as described above may be applied to the heat-developable image recording layer, the component layer of the heat-development-type image recording material of the present invention.

Further, as another method of preparation of the light-sensitive silver halide, a light-sensitive silver salt forming component may be made present together with an organic silver salt to thereby form a light-sensitive silver halide upon part of the organic silver salt. The light-sensitive silver salt forming component usable in this preparation includes inorganic halides such as, e.g., halides represented by MXn (wherein M is hydrogen, NH$_4$ group or a metallic atom, X is Cl, Br or I, and n is 1 when M is hydrogen or NH$_4$ group and when M is a metallic atom, n is the valence thereof, the metallic atom including lithium, sodium, potassium, rubidium, cesium, copper, gold, beryllium, magnesium, calcium, strontium, barium, zinc, cadmium, mercury, aluminum, indium, lanthanum, ruthenium, thallium, germanium, tin, lead, antimony, bismuth, chromium, molybdenum, tungsten, manganese, rhenium, iron, cobalt, nickel, rhodium, palladium, osmium, iridium, platinum, cerium, and the like); halogen-containing metallic complex (such as $K_2PtCl_6$, $K_2PtBr_6$, $HAuCl_4$, $(NH_4)_2IrCl_6$, $(NH_4)_3IrCl_6$, $(NH_4)_2RuCl_6$, $(NH_4)_3RuCl_6$, $(NH_4)_3RhBr_6$, and the like); onium halides (e.g., quaternary ammonium halides such as tetramethyl-ammonium bromide, trimethyl-phenyl-ammonium bromide, cetyl-ethyl-dimethylammonium bromide, 3-methyl-thiazolium bromide, trimethyl-benzylammonium bromide, etc., quaternary phosphonium halides such as tetraethyl-phosphonium bromide, etc., tertiary sulfonium halides such as benzyl-ethyl-methyl bromide, 1-ethyl-thiazolium bromide, etc.); halogenated hydrocarbons (such as, e.g., iodoform, bromoform, carbon tetrabromide, 2-bromo-2-methylpropane, etc.); N-halogenated compounds (such as, e.g., N-chlorosuccinic acid imide, N-bromophthalic acid imide, N-bromoacetamide, N-iodosuccinic acid imide, N-bromophthalazinone, N-chlorophthalazinone, N-bromoacetanilide, N,N-dibromobenzenesulfonamide, N-bromo-N-methylbenzenesulfonamide, 1,3-dibromo-4,4-dimethylhydantoin, etc.); and other halogen-containing compounds (such as, e.g., triphenyl-methyl chloride, triphenyl-methyl bromide, 2-bromobutyric acid, 2-bromoethanol, etc.); and the like.

These light-sensitive silver halides and light-sensitive silver salt forming components may be used in combination in various manners, and the using quantity thereof is from 0.001 to 1.0 mole and preferably from 0.01 to 0.3 mole per mole of the organic silver salt.

The (c) binder to be contained in the heat-development-type image recording layer of the present invention may be either a hydrophobic or hydrophilic material and also may be either transparent or semitransparent, examples of which are synthetic or natural various macromolecular materials such as polyvinyl butyral, polyvinyl acetate, ethyl cellulose, polymethyl methacrylate, cellulose acetate, cellulose acetate-butyrate, polyvinyl alcohol, gelatin, gelatin derivatives, and the like.

Derivatives of the 3-amino-5-mercapto-1,2,4-triazole and 2-amino-5-mercapto-1,3,4-thiadiazole which have substituents in the amino group thereof, the compounds having the foregoing Formula [I], which are the marked characteristic to be contained in the heat-development-type image recording layer in the present invention, are described below:

In Formula [I], as the alkyl radical which may be allowed to have a substituent, $R^1$ and $R^2$ each represents an alkyl radical in the straight chain, branched chain or cyclic form and having from 1 to 20 carbon atoms, and examples of the alkyl radicals are methyl, ethyl, propyl, butyl, pentyl, hexyl, heptyl, nonyl, undecyl, tridecyl, pentadecyl, heptadecyl, nonadecyl, isopentyl, tert-butyl, cyclohexyl, benzyl, 3-hydroxypropyl, dichloromethyl, trifluoromethyl radicals and the like.

As the alkenyl radical which may be allowed to have a substituent, $R^1$ and $R^2$ each represents an alkenyl radical in the straight chain form and having from 2 to 12 carbon atoms, and examples of the alkenyl radical are vinyl, 1-propenyl, 2-propenyl, 1,3-butadienyl, 2-pentenyl-3-hydroxy-1-propenyl, 2-chloro-2-propenyl radicals and the like.

As the aryl radical which may be allowed to have a substituent, $R^1$ and $R^2$ each represents an aryl radical examples of which are phenyl, p-nitrophenyl, m-chlorophenyl, m-carboxyphenyl, p-methoxyphenyl, p-aminophenyl, pyridyl radicals and the like.

And the alkoxy radical which may be allowed to have a substituent includes methoxy, ethoxy, isopropoxy, tert-butoxy, 2-nitroethoxy, 2-chloroethoxy radicals and the like.

The following are examples of those compounds having Formula [I] of the present invention:

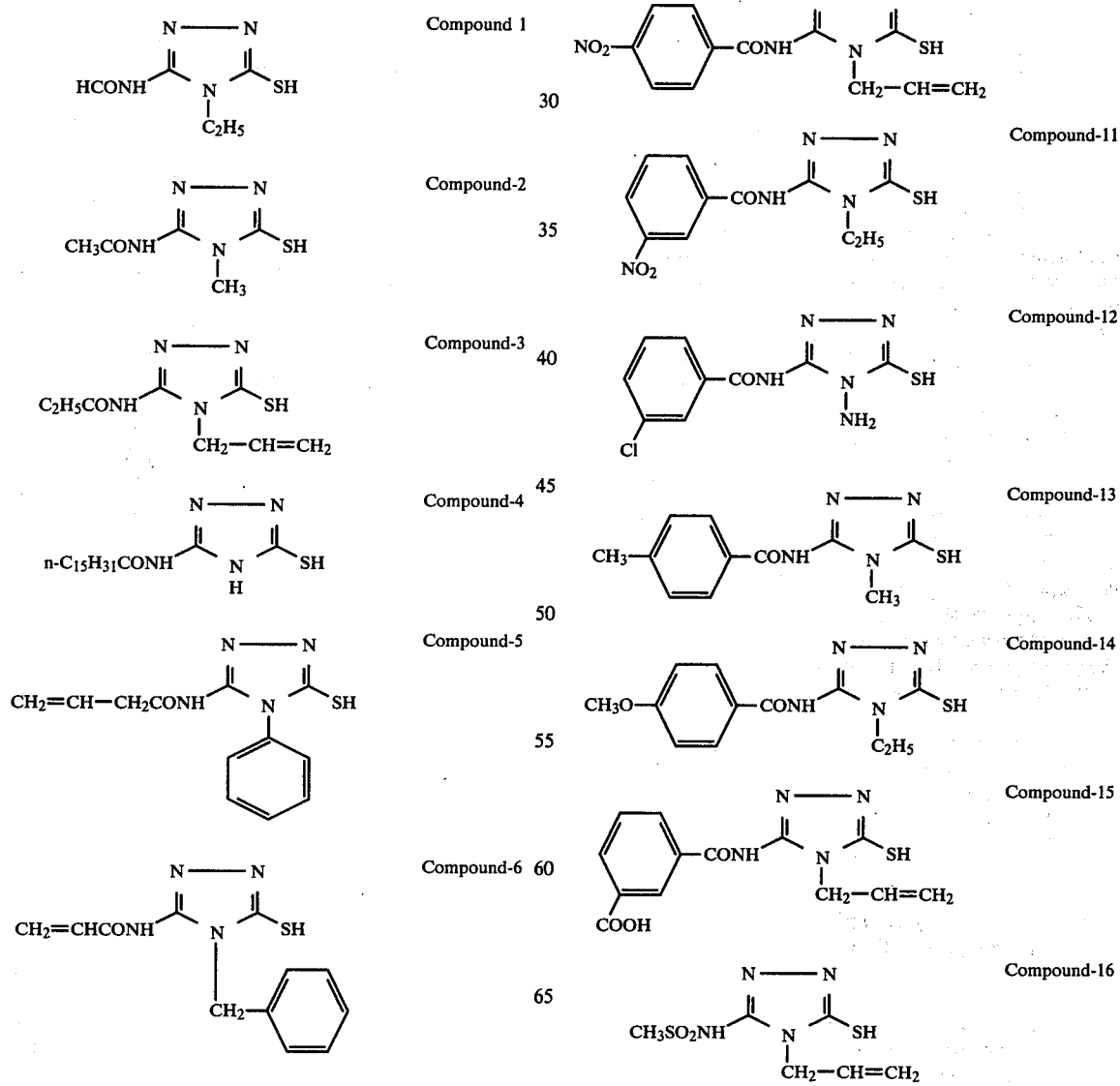

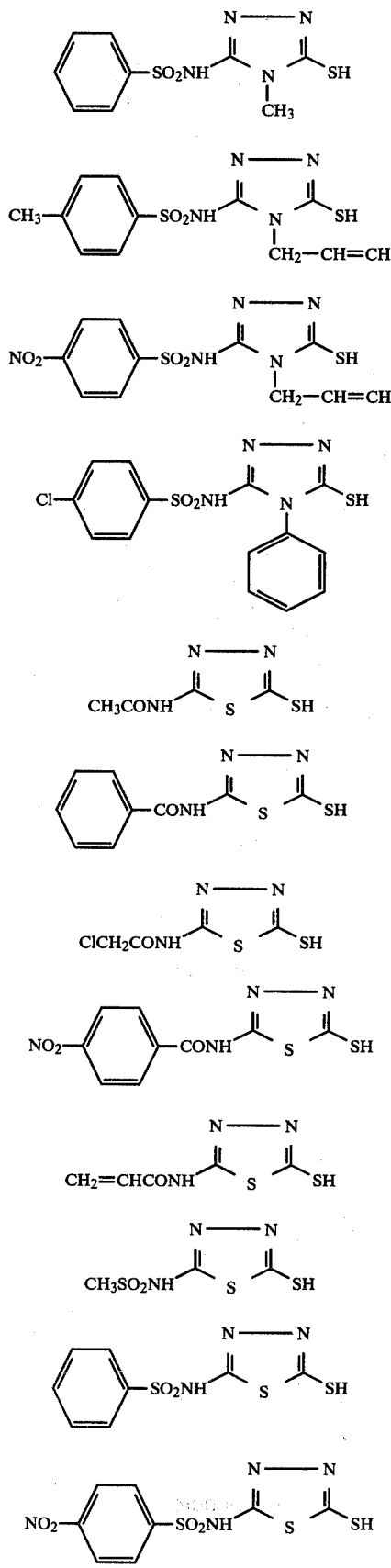

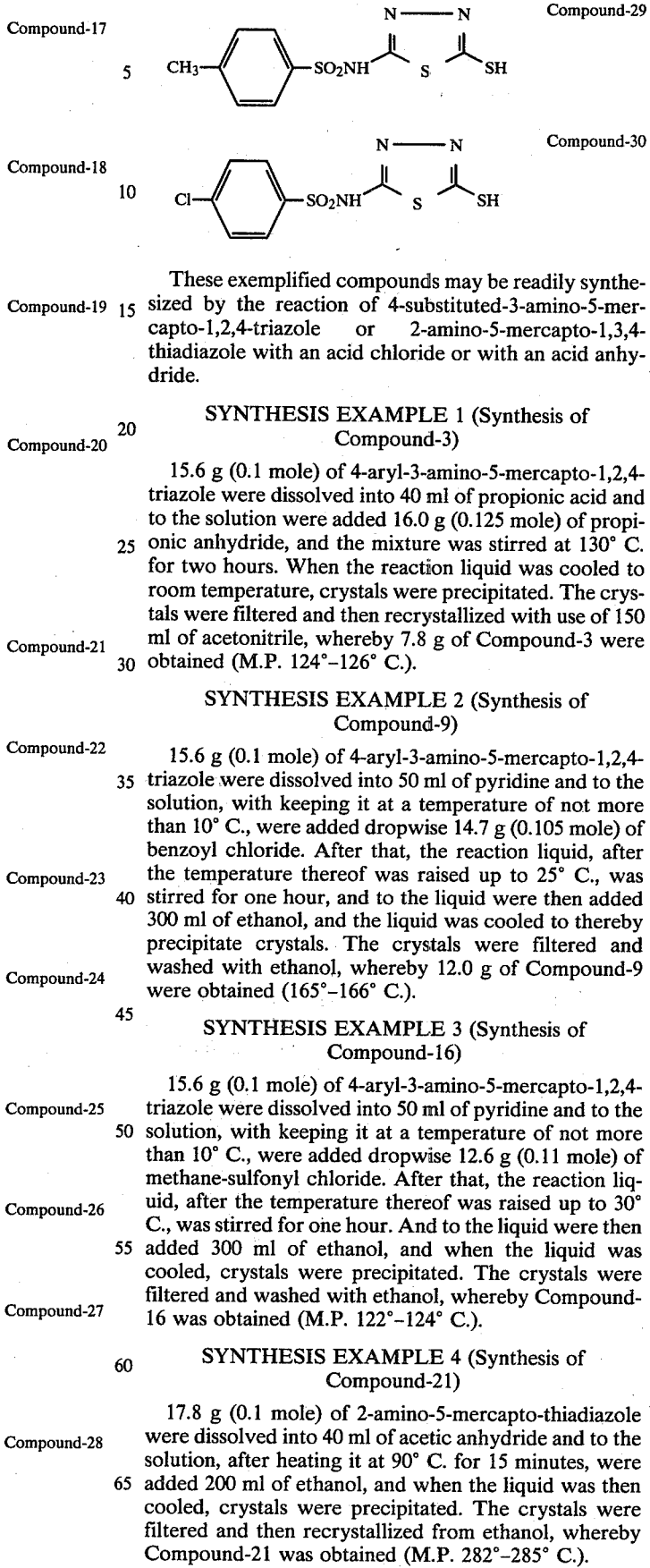

These exemplified compounds may be readily synthesized by the reaction of 4-substituted-3-amino-5-mercapto-1,2,4-triazole or 2-amino-5-mercapto-1,3,4-thiadiazole with an acid chloride or with an acid anhydride.

SYNTHESIS EXAMPLE 1 (Synthesis of Compound-3)

15.6 g (0.1 mole) of 4-aryl-3-amino-5-mercapto-1,2,4-triazole were dissolved into 40 ml of propionic acid and to the solution were added 16.0 g (0.125 mole) of propionic anhydride, and the mixture was stirred at 130° C. for two hours. When the reaction liquid was cooled to room temperature, crystals were precipitated. The crystals were filtered and then recrystallized with use of 150 ml of acetonitrile, whereby 7.8 g of Compound-3 were obtained (M.P. 124°–126° C.).

SYNTHESIS EXAMPLE 2 (Synthesis of Compound-9)

15.6 g (0.1 mole) of 4-aryl-3-amino-5-mercapto-1,2,4-triazole were dissolved into 50 ml of pyridine and to the solution, with keeping it at a temperature of not more than 10° C., were added dropwise 14.7 g (0.105 mole) of benzoyl chloride. After that, the reaction liquid, after the temperature thereof was raised up to 25° C., was stirred for one hour, and to the liquid were then added 300 ml of ethanol, and the liquid was cooled to thereby precipitate crystals. The crystals were filtered and washed with ethanol, whereby 12.0 g of Compound-9 were obtained (165°–166° C.).

SYNTHESIS EXAMPLE 3 (Synthesis of Compound-16)

15.6 g (0.1 mole) of 4-aryl-3-amino-5-mercapto-1,2,4-triazole were dissolved into 50 ml of pyridine and to the solution, with keeping it at a temperature of not more than 10° C., were added dropwise 12.6 g (0.11 mole) of methane-sulfonyl chloride. After that, the reaction liquid, after the temperature thereof was raised up to 30° C., was stirred for one hour. And to the liquid were then added 300 ml of ethanol, and when the liquid was cooled, crystals were precipitated. The crystals were filtered and washed with ethanol, whereby Compound-16 was obtained (M.P. 122°–124° C.).

SYNTHESIS EXAMPLE 4 (Synthesis of Compound-21)

17.8 g (0.1 mole) of 2-amino-5-mercapto-thiadiazole were dissolved into 40 ml of acetic anhydride and to the solution, after heating it at 90° C. for 15 minutes, were added 200 ml of ethanol, and when the liquid was then cooled, crystals were precipitated. The crystals were filtered and then recrystallized from ethanol, whereby Compound-21 was obtained (M.P. 282°–285° C.).

The using quantity of these compounds having Formula [I], although different according to the kind of the organic silver salt used, the kind of the reducing agent used, and the like, is preferably from 0.001 mole to 10 moles and particularly preferably from 0.005 mole to 0.5 mole per mole of the organic silver salt used.

To the heat-development-type image recording material of the present invention may be applied toning agents for the purpose of sufficiently blackening the image.

Those applicable toning agents include those derivatives of such compounds as, e.g., phthalimide, pyrazolone, quinazoline, N-hydroxynaphthalimide, benzoxazine, naphthoxazinedione, 2,3-dihydro-phthalazindione, 2,3-dihydro-1,3-oxazine-2,4-dione, oxypyridine, aminopyridine, hydroxyquinoline, aminoquinoline, isocarbostyryl, sulfonamide, 2H-1,3-benzothiazine-2,4-(3H)-dione, benzotriazine, mercaptotriazole, dimercaptotetrazapentalene, phthalic acid, phthalazine, naphthalic acid, phthalamic acid, phthalazinone, and the like, which are the compounds as described in Japanese Patent O.P.I. Publication Nos. 4928/1971, 6077/1971, 5019/1974, 5020/1974, 91215/1974, 107727/1974, 2524/1975, 67132/1975, 67641/1975, 114217/1975, 33722/1977, 99813/1977, 1020/1978, 55115/1978, 76020/1978, 125014/1978, 156523/1979, 156524/1979, 156525/1979, 156526/1979, 4060/1980, 4061/1980, 32015/1980 and the like, and West German Pat. Nos. 2,140,406, 2,147,063 and 2,220,618, and U.S. Pat. Nos. 3,080,254, 3,847,612, 3,782,941, 3,949,732, 4,123,282, and 4,201,582, and the like.

Further, the heat-development-type image recording material of the present invention may contain those additives having the following Formula [II] for the purpose of development acceleration, tone improvement, and the like:

$$R^3-S+C\!\!+_m\!\!-COZ \quad \text{(with } R^4, R^5 \text{ on C)} \quad \text{Formula [II]}$$

wherein $R^3$ represents an alkyl, an aryl or a heterocyclic radical, the radicals each being allowed to have a substituent; $R^4$ and $R^5$ may be either the same or different and each represents hydrogen, an alkyl, an aryl or a heterocyclic radical, the radicals each being allowed to have a substituent; Z is hydroxyl or amino radical; and m is an integer of 1 or 2.

The $R^3$ in Formula [II] is preferably an alkyl radical (substituted or not) having from 1 to 7 carbon atoms such as, e.g., ethyl, hydroxyethyl, carboxymethyl, carbamoylmethyl, benzyl, or the like; an aryl radical (substituted or not) such as, e.g., phenyl, tolyl, carboxyphenyl, carbamoylphenyl, hydroxyphenyl, methylthiophenyl, or the like; or a heterocyclic radical such as, e.g., thienyl, benzothienyl, furyl, pyranyl, chromenyl, pyrolyl, imidazolyl, pyridyl, pyrazyl, pyrimidinyl, indolidinyl, isothiazoyl, isooxazolyl, furazanyl, isochromanyl, pyrrolidinyl, 2-benzothiazolyl, 2-benzimidazolyl, 1-phenyl-5-triazolyl, 2-thiadiazolyl, or the like.

The $R^4$ and $R^5$ each is preferably hydrogen or a lower alkyl (e.g. methyl group, ethyl group), and more preferably hydrogen.

The following are examples of these additives having Formula [II]:

| | |
|---|---|
| $C_2H_5SCH_2COOH$ | 1. |
| $HOCH_2CH_2SCH_2COOH$ | 2. |
| 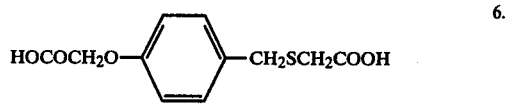 | 3. |
| $HOCH_2CH_2SCH_2CONH_2$ | 4. |
|  | 5. |
|  | 6. |
| 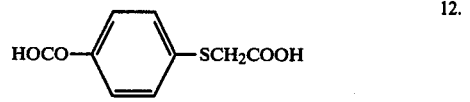 | 7. |
| $HOCOCH_2SCH_2COOH$ | 8. |
| $NH_2COCH_2SCH_2CONH_2$ | 9. |
|  | 10. |
|  | 11. |
| 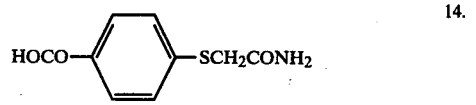 | 12. |
|  | 13. |
| 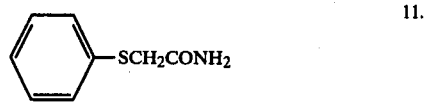 | 14. |
| 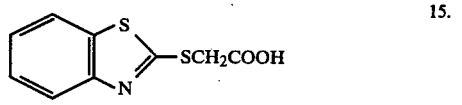 | 15. |
| 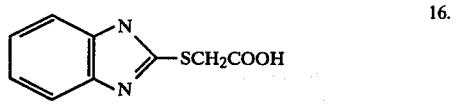 | 16. |

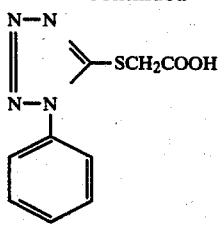 13.

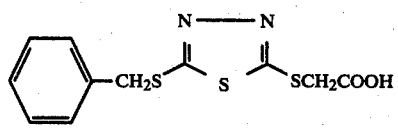 14.

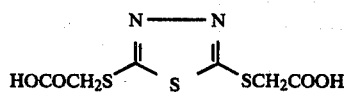 15.

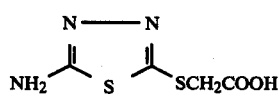 16.

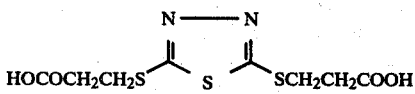 17.

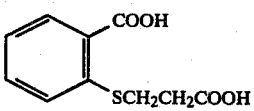 18.

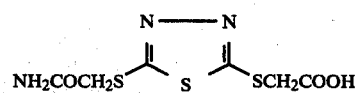 19.

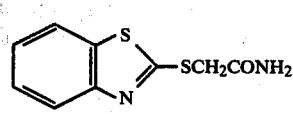 20.

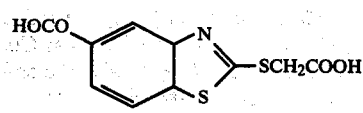 21.

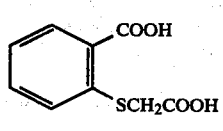 22.

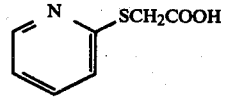 23.

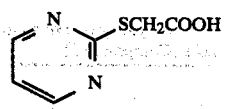 24.

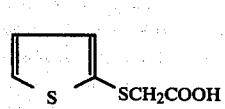 25.

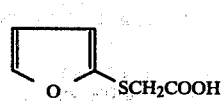 26.

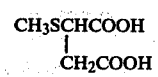 27.

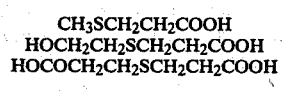 28.

CH$_3$SCHCOOH
|
CH$_2$COOH

29.

CH$_3$SCH$_2$CH$_2$COOH  30.
HOCH$_2$CH$_2$SCH$_2$CH$_2$COOH  31.
HOCOCH$_2$CH$_2$SCH$_2$CH$_2$COOH  32.

33.

34.

The using quantity of these additives having Formula [II], although different according to the kind of the organic silver salt used and to the kind of the reducing agent used, is preferably from 0.001 mole to 10 moles and more preferably from 0.1 mole to 2 moles per mole of the organic silver salt used.

The heat-development-type image recording material may also contain an antifoggant for the purpose of preventing possible occurrence of fog by heating. As the antifoggant, those compounds may be used which include mercuric salts; oxidizing agents such as, e.g., N-halogenoacetamide, N-halogenosuccinic acid imide, perchloric acid and the salts thereof, inorganic peroxides, persulfates, and the like; acids and the salts thereof such as, e.g., sulfinic acid, lithium laurate, rosin, diterpenic acid, thiosulfonic acid, and the like; sulfur-containing compounds such as, e.g., mercapto compound-releasable compounds, thiouracil, disulfides, sulfur simple substance, mercapto-1,2,4-triazole, thiazolinethione, polysulfide compounds, and the like; and other compounds such as oxazoline, 1,2,4-triazole, phthalimide, and the like, which are the compounds described in Japanese Patent Examined Publication No. 11113/1972, Japanese Patent O.P.I. Publication Nos. 90118/1974, 10724/1974, 97613/1974, 101019/1975, 130720/1974, 123331/1975, 47419/1976, 57435/1976, 78227/1976, 104338/1976, 19825/1978, 20923/1978, 50725/1976, 3223/1976, 42529/1976, 81124/1976, 51821/1979, 93149/1980, and the like, and British Pat. No. 1,455,271, U.S. Pat. Nos. 3,885,968, 3,700,457, 4,137,079 and 4,138,265, and West German Pat. No. 2,617,907, and the like.

The heat-development-type image recording material of this invention may also contain a compound capable of releasing water by heating, i.e., a water-releasable compound. Such water-releasable compounds include such compounds containing water of crystallization as, e.g., trisodium phosphate dodeca-hydrated, sodium sulfate deca-hydrated, iron-ammonium sulfate hexahydrated, ammonium alum tetracosa-hydrated, potassium alum tetracosa-hydrated, magnesium acetate tetrahydrated, manganese acetate tetra-hydrated, and the like.

The heat-development-type image recording material of this invention may further contain in the image recording layer thereof a water-retainable compound for the purpose of retaining the water content of a given level. Such water-retainable compounds include polyalkylene oxide (polyglycol), hydroxyethyl cellulose, carboxymethyl cellulose, and the like, as described in U.S. Pat. No. 3,347,675.

In the heat-development-type image recording material of this invention, in addition to the above components, may, if necessary, be incorporated various known additives such as a spectrally sensitizing dye, antihalation dye, anti-printout agent, and the like.

The above-described spectrally sensitizing dye includes merocyanine, rhodacyanine, styryls, and the like, which are useful for silver halide emulsions.

The anti-printout agent includes tetrabromobutane, tribromoethanol, 2-bromo-2-tolylacetamide, 2-bromo-2-tolylsulfonylacetamide, 2-tribromomethylsulfonylbenzothiazole, 2,4-bis(tribromomethyl)-6-methyltriazine, and the like.

Materials usable as the support of the heat-development-type image recording material of this invention include synthetic plastic films such as, e.g., polyethylene film, cellulose acetate film, polyethylene terephthalate film, etc., glass, metals, photographic paper, printing paper, baryta paper, resin-coated paper, and the like. These support materials may have a subbing layer thereon.

In the case where the heat-development-type image recording material of the present invention is used as an electro-thermo recording material, the support is desirable to be conductive. The conductive support material includes those materials produced by providing a conductive coat on a base plate such as, e.g., plastic film, a glass plate, etc.; those materials whose base plate itself is conductive like a metal plate; and the like. Because paper is treatable to be in whenever form, the paper appropriately treated may be used as the above-mentioned support. Providing conductivity on the surface of such a base plate as plastic film, glass, etc., may be attained in such a manner that the base plate is formed on the surface thereof with stratified metal foil layers or with a conductive coat by means of vacuum deposition, cathode sputtering, ion-plating, electroless plating, or the like.

The respective components (a)-(d) to be used in the heat-development-type image recording material of the invention are coated together with a binder prepared by dissolving a binder material into water, an organic solvent or a mixture of water with an organic solvent on any of the above-described support to thereby form a heat-developable image recording layer. The dried thickness of the image recording layer is from 1 to 1000μ, and preferably from 3 to 20μ. If necessary, the final coating may be provided on the image recording layer.

In addition, part of the respective components (a)-(d) may be allowed to ooze out of the heat-developable image recording layer to permeate into the support. Further, part of the respective components (a)-(d) may be allowed to ooze out of the layer to permeate into the above-mentioned final layer and/or the subbing layer.

If the thus produced heat-development-type image recording material of this invention is a light-sensitive material, the material, after being exposed to light, is developed by heating at a temperature of from 80° C. to 200° C. for a period of from 1 to 60 seconds. If necessary, the development may be made with the recording material brought into contact with a water-impermeable material. Further, if necessary, the recording material may be subjected to preheating at a temperature of from 70° C. to 180° C. before exposure. The light source for use in the above-mentioned exposure includes a glow lamp, tungsten lamp, fluorescent lamp, mercury vapor lamp, iodine lamp, xenon lamp, LED light source, CRT light source, laser light source, and the like.

If the heat-development-type image recording material of the present invention is an electro-thermo recording material, the material, after being energized imagewise to form a latent image by an appropriate means, is developed by heating at a temperature of from 80° C. to 200° C. for a period of from 1 to 60 seconds. The development may also be made concurrently with the energizing. As the energizing method, various devices for controlling the flow of current are conceivable. Such devices include, e.g., a charged stencil, needle or screen, a glid controll discharger, an appropriate photoconductive layer contiguous to the image recording layer, and the like. In the case of using a photoconductor for the control of current, various kinds of exposure apparatus may be used by arbitrarily selecting a photoconductor. Such exposure apparatus may use any of light sources such as a tungsten lamp, xenon lamp, light emission diode, laser beam, infrared rays and X rays. As the light source, any radiant light source, if the photoconductor reacts to the radiation generated therefrom, may be used.

The present invention will be illustrated in detail in reference to the following examples, but the embodiment of the present invention is not limited thereto.

EXAMPLE 1

18.9 g (0.11 mole) of 5-nitrobenzotriazole were dissolved into 300 ml of ethanol and to the solution were added dropwise a solution of 16.9 g (0.10 mole) of silver nitrate dissolved into 100 ml of water, and the mixture was stirred for 30 minutes. The resulting crystals were filtrated and then washed with 100 ml of ethanol, thereby obtaining 26.4 g of silver salt of 5-nitrobenzotriazole.

To 13.5 g of the thus obtained silver salt of 5-nitrobenzotriazole were added 200 ml of ethanol and 250 ml of a 16% aqueous polyvinylbutyral solution (Eslec W-201, product of Sekisui Chemical Co., Ltd.), and the mixture was dispersed by means of a ball mill to thereby prepare a dispersed liquid. To the resulting dispersed liquid, with stirring, were added the following components in the order described, whereby a coating liquid was prepared.

| Component-1: | |
|---|---|
| Ascorbic acid (20% aqueous solution) | 38 ml |
| Component-2: | |
| Phthalic acid (10% methanol solution) | 40 ml |
| Component-3: | |
| Phthalazine (20% methanol solution) | 15 ml |
| Component-4: | |
| 2% methanol solution of 4-aryl-3-propionamido-5-mercapto-1,2,4-triazole (Compound-3) | 10 ml |

The thus prepared coating liquid was coated on a transparent conductive film support (electrode grade: surface resistivity 500 Ω/cm$^2$, produced by Teijin, Ltd.) so that the quantity of silver per m$^2$ is 0.90 g, thereby producing a heat-development-type image recording material (hereinafter referred to as the recording material)-1.

And a recording material-2 was prepared in quite the same manner as in above with the exception that in place of the foregoing Compound-4 11.5 ml of a 2% methanol solution of 4-aryl-3-benzoylamino-5-mercapto-1,2,4-triazole (Compound-9) was used.

Further, in the identical manner, 13.0 ml of a 2% methanol solution of 4-aryl-3p-nitrobenzoylamino-5-mercapto-1,2,4-triazole (Compound-10) was used to prepare a recording material-3, 11.5 ml of a 2% methanol solution of 4-aryl-3-methanesulfonamido-5-mercapto-1,2,4-triazole (Compound-16) was used to prepare a recording material-4, and 10 ml of a 2% methanol solution of 2-p-nitrobenzoylamino-5-mercapto-1,3,4-thiadiazole (Compound-24) was used to prepare a recording material-5.

And for comparison a recording material-6 was prepared in the identical manner with the above with the exception that in place of the foregoing Component-4, 9.5 ml of a 2% methanol solution of 4-aryl-3-mercapto-1,2,4-triazole, and a recording material-7 was prepared likewise by use of 8 ml of a 2% methanol solution of 2-mercapto-5-amino-1,3,4-thiadiazole. And further, a recording material-8 was prepared likewise except that no compound corresponding to Component-4 was used.

An electrode composed of a 1 cm × 1 cm size metallic copper plate on an insulating plate was brought into contact with each of the thus prepared recording materials 1 to 8 and the copper plate was kept at a positive potential of 100 V to the conductive layer of the recording material, and energized for 1 second. After the energizing, the recording material and the metallic copper plate were separated.

Next, the same operation was repeated, making the potential of the copper plate zero Volt to the conductive layer.

Subsequently, these recording materials were heated to be developed for 10 seconds at a temperature of 140° C. on a heated platen. As the result, an image appeared on the energized area of the recording material that was energized by making the potential positive 100 V, while no image appeared where the potential was zero Volt.

The respective transmission optical densities are as follows:

TABLE 1

| Sample No. | Additive compound | Density at potential 0 V | Density at potential 100 V |
|---|---|---|---|
| 1 | Compound-3 | 0.03 | 0.91 |
| 2 | Compound-9 | 0.02 | 0.99 |
| 3 | Compound-10 | 0.02 | 0.82 |
| 4 | Compound-16 | 0.03 | 0.78 |
| 5 | Compound-24 | 0.02 | 0.63 |
| 6 | 4-aryl-3-mercapto-1,2,4-triazole | 0.03 | 0.06 |
| 7 | 2-mercapto-5-amino-1,3,4-thiadiazole | 0.02 | 0.18 |
| 8 | None | 0.04 | 0.08 |

The densities in the above table are values each relative to the density regarded as 0 of each recording material when subjected to no energizing nor heating.

EXAMPLE 2

To a solution of 54.4 g of behenic acid dissolved into 1200 ml of toluene were added 2400 ml of water, and the mixture liquid was homogenized by a high-speed homogenizer. To this solution, with stirring, were added dropwise spending about 30 minutes 400 ml of an aqueous ammoniacal silver nitrate solution containing 27.7 g of silver nitrate, with keeping the temperature of the reaction liquid at 60° C. The stirring was further continued for another 30 minutes. The resulting crystals were filtrated, washed with water, washed with methanol, and then dried under reduced pressure, whereby 65.0 g of silver behenate were obtained.

To 22.2 g of the obtained silver behenate were added 420 ml of ethanol and 40 g of polyvinyl butyral (Eslec BL-1, produced by Sekisui Chemical Co., Ltd.), and the mixture was dispersed by a ball mill spending about 24 hours to prepare a dispersed liquid. To this dispersed liquid, with stirring, were then added the following components in the order described below to thereby prepare a coating liquid.

| Component-1: | |
|---|---|
| Ascorbic acid monopalmitate (20% ethanol solution) | 50 ml |
| Component-2: | |
| Phthalic acid (10% methanol solution) | 40 ml |
| Component-3: | |
| Phthalazine (20% methanol solution) | 15 ml |
| Component-4: | |
| 4-aryl-3-propionamido-5-mercapto-1,2,4-triazole (Compound-3) (2% methanol solution) | 10 ml |

The thus prepared coating liquid was coated on a transparent conductive film support (electrode grade: surface resistivity 500 $\Omega/cm^2$, manufactured by Teijin, Ltd.) so that the quantity of silver per $m^2$ is 0.90 g, whereby a recording material-9 was produced.

And a recording material-10 was prepared in the identical manner with the exception that in place of the foregoing Component-4 11.5 ml of a 2% methanol solution of 4-aryl-3-benzoylamino-5-mercapto-1,2,4-triazole (Compound-9) was used.

Further, in the identical manner, a recording material-11 was prepared by use of 13.0 ml of a 2% methanol solution of 4-aryl-3-p-nitrobenzoylamino-5-mercapto-1,2,4-triazol (Compound-10), a recording material-12 was prepared by use of 11.5 ml of a 2% methanol solution of 4-aryl-3-methanesulfoneamido-5-mercapto-1,2,4-triazole (Compound-16), and a recording material-13 was prepared by use of 10 ml of a 2% methanol solution of 2-p-nitrobenzoylamino-5-mercapto-1,3,4-thiadiazole (Compound-24).

Further, for comparison, a recording material-14 was prepared in the identical manner with the above with the exception that in place of the foregoing Component-4, 9.5 ml of a 2% methanol solution of 4-aryl-3-mercapto-1,2,4-triazole was used. Likewise, a recording material-15 was prepared by use of 8 ml of a 2% methanol solution of 2-mercapto-5-amino-1,3,4-thiadiazole, and a recording material-16 was prepared without use of any compound in place of Component-4.

The thus prepared recording materials-9 to -16 were tested in quite the same manner as in Example 1 with the exception that the developing temperature was changed to 110° C. The obtained test results are as shown in Table 2.

TABLE 2

| Sample No. | Additive compound | Density at potential 0 V | Density at potential 100 V |
|---|---|---|---|
| 9 | Compound-3 | 0.24 | 0.98 |
| 10 | Compound-9 | 0.23 | 1.03 |
| 11 | Compound-10 | 0.24 | 0.92 |
| 12 | Compound-16 | 0.22 | 0.87 |
| 13 | Compound-24 | 0.23 | 0.72 |
| 14 | 4-aryl-3-mercapto-1,2,4-triazole | 0.25 | 0.31 |
| 15 | 2-mercapto-5-amino-1,3,4-thiadiazole | 0.27 | 0.40 |
| 16 | None | 0.26 | 0.32 |

The densities in the above table are values each relative to the density regarded as 0 of each recording material when subjected to no energizing nor heating.

EXAMPLE 3

To 13.5 g of silver salt of 5-nitrobenzotriazole were added 200 ml of ethanol and 250 ml of an aqueous 8% polyvinylbutyral solution (Eslec W-201, produced by Sekisui Chemical Co., Ltd.) and the mixture was dispersed for a period of 24 hours by means of a ball mill to thereby prepare a dispersed liquid. To this dispersed liquid, with stirring, were added the following components in the order described below, thereby preparing a coating liquid.

Component-1:
  13 ml of a silver iodide emulsion (cubic crystal emulsion which contains 60 g of gelatin and 0.38 mole of silver per kg of emulsion and average crystal size is 0.1 micron)

Component-2:
  3.8 ml of a sensitizing dye (0.05% by weight methanol solution of a merocyanine dye having the next formula:)

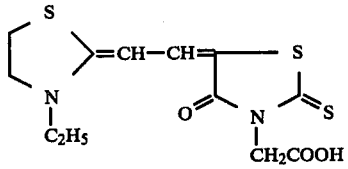

Component-3:
  38 ml of ascorbic acid (20% aqueous solution)

Component-4:
  40 ml of phthalic acid (10% methanol solution)

Component-5:
  15 ml of phthalazine (20% methanol solution)

Component-6:
  11.5 ml of 4-aryl-3-benzoylamino-5-mercapto-1,2,4-triazole (Compound-9)(2% methanol solution)

The thus prepared coating liquid was coated on a photographic paper support so that the quantity of silver per m$^2$ is 0.5 g, whereby a recording material-17 was prepared.

And a recording material-18 was prepared in the identical manner with the above with the exception that in place of the foregoing Component-6, 10 ml of a 2% methanol solution of 4-aryl-3-propionamido-5-mercapto-1,2,4-triazole (Compound-3) were used. Further, in the identical manner, a recording material-19 was prepared by use of 13.0 ml of a 2% methanol solution of 4-aryl-3-p-nitrobenzoylamino-5-mercapto-1,2,4-triazole (Compound-10), a recording material-20 was prepared by use of 11.5 ml of a 2% methanol solution of 4-aryl-3-methanesulfonamido-5-mercapto-1,2,4-triazole (Compound-16), and a recording material-21 was prepared by use of 10 ml of a 2% methanol solution of 2-p-nitrobenzoylamino-5-mercapto-1,3,4-thiadiazole (Compound-24).

And, for comparison, a recording material-22 was prepared in the identical manner with the above except that in place of the foregoing Component-6, 9.5 ml of a 2% methanol solution of 4-aryl-3-mercapto-1,2,4-triazole were used, and a recording material-23 was prepared likewise by use of 8 ml of a 2% methanol solution of 2-mercapto-5-amino-1,3,4-thiadiazole. Further, a recording material-24 was prepared in like manner except that no compound corresponding to Component-6 was used.

Each of the thus prepared recording materials-17 to -24 was exposed through a step wedge to a white light in the quantity of light of 160 CMS (candela-meter-second), and then heated to be developed at 120° C. for 10 seconds. The obtained results are as shown in Table 3.

In order to test the preservability of these recording materials, each of the recording materials-17 to -24 was allowed to stand over a period of 24 hours under a 1000-lux white fluorescent lamp light to examine the increase in the minimum density by the print-out effect. The obtained results are as shown in the parentheses in the "Minimum density" column of Table 3.

TABLE 3

| Sample No. | Additive compound | Maximum density | Minimum density | Speed (Note 1) |
|---|---|---|---|---|
| 17 | Compound-9 | 1.25 | 0.05(0.06) | 280 |
| 18 | Compound-3 | 1.32 | 0.04(0.05) | 298 |
| 19 | Compound-10 | 1.21 | 0.04(0.05) | 248 |
| 20 | Compound-16 | 1.19 | 0.05(0.06) | 212 |
| 21 | Compound-24 | 1.26 | 0.05(0.06) | 264 |
| 22 | 4-aryl-3-mercapto-1,2,4-triazole | 0.72 | 0.04(0.12) | 84 |
| 23 | 2-mercapto-5-amino-1,3,4-thiadiazole | 0.85 | 0.07(0.14) | 112 |
| 24 | None | 0.81 | 0.06(0.15) | 100 |

(Note 1):
The speed values shown in the above table are relative values to the speed regarded as 100 of the comparative recording material-24.

As apparent from Table 3, the samples of the present invention show not only satisfactory maximum densities and speeds but also excellent preservability.

EXAMPLE 4

To 22.2 g of silver behenate were added 200 ml of ethanol and 250 ml of an aqueous 8% polyvinyl butyral solution (Eslec W-201, produced by Sekisui Chemical Co., Ltd.), and the mixture was dispersed over a period of 24 hours by means of a ball mill to thereby prepare a dispersed liquid. To this dispersed liquid, with stirring, were added the following components in the order described below, thereby preparing a coating liquid.

Component-1:
  13 ml of a silver bromide emulsion (cubic crystal emulsion which contains 60 g of gelatin and 0.38 mole of silver per kg of emulsion and average crystal size is 0.1 micron)

Component-2:
  3.8 ml of a sensitizing dye (0.05% by weight methanol solution of a merocyanine dye having the following formula:)

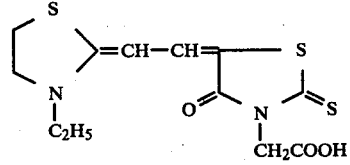

Component-3:
  38 ml of ascorbic acid (20% aqueous solution)

Component-4:
  40 ml of phthalic acid (10% methanol solution)

Component-5:
  15 ml of phthalazine (20% methanol solution)

Component-6:

10 ml of 4-aryl-3-propionamido-5-mercapto-1,2,4-triazole (Compound-3)(2% methanol solution)

The thus prepared coating liquid was coated on a photographic paper support so that the quantity of silver per m² is 0.48 g, whereby a recording material-25 was produced. And a recording material-26 was prepared in the identical manner except that in place of the above Component-6, 11.5 ml of a 2% methanol solution of 4-aryl-3-benzoylamino-5-mercapto-1,2,4-triazole (Compound-9) were used. Further, in the identical manner, a recording material-27 was prepared by use of 13.0 ml of a 2% methanol solution of 4-aryl-3-p-nitrobenzoylamino-5-mercapto-1,2,4-triazole (Compound-10), a recording material-28 was prepared by use of 11.5 ml of a 2% methanol solution of 4-aryl-3-methanesulfonamido-5-mercapto-1,2,4-triazole (Compound-16), and a recording material-29 was prepared by use of 10 ml of a 2% methanol solution of 2-p-nitrobenzoylamino-5-mercapto-1,3,4-thiadiazole (Compound-24).

Further, for comparison, a recording material-30 was prepared in the identical manner except that in place of the foregoing Component-6, 9.5 ml of a 2% methanol solution of 4-aryl-3-mercapto-1,2,4-triazole, and a recording material-31 was prepared likewise by use of 8 ml of a 2% methanol solution of 2-mercapto-5-amino-1,3,4-thiadiazole, and further a recording material-32 was prepared in the same manner except that no compound corresponding to Component-6 was used.

Each of the thus prepared recording materials-25 to -32 was exposed through a step wedge to a white light in the quantity of light of 160 CMS, and then heated to be developed at 100°0 C. for 10 seconds. The obtained results are as shown in Table 4.

TABLE 4

| Sample No. | Additive compound | Maximum density | Minimum density | Speed (Note 2) |
|---|---|---|---|---|
| 25 | Compound-3 | 1.26 | 0.24 | 204 |
| 26 | Compound-9 | 1.20 | 0.22 | 198 |
| 27 | Compound-10 | 1.24 | 0.23 | 188 |
| 28 | Compound-16 | 1.18 | 0.25 | 192 |
| 29 | Compound-24 | 1.18 | 0.24 | 190 |
| 30 | 4-aryl-3-mercapto-1,2,4-triazole | 0.63 | 0.26 | 72 |
| 31 | 2-mercapto-5-amino-1,3,4-thiadiazole | 0.98 | 0.30 | 118 |
| 32 | None | 0.92 | 0.28 | 100 |

(Note 2):
The speed values shown in the table are relative values to the speed regarded as 100 of the comparative recording material-32.

EXAMPLE 5

To 13.5 g of silver salt of 5-nitrobenzotriazole were added 420 ml of ethanol and 20 g of polyvinyl butyral (Eslec BL-1, produced by Sekisui Chemical Co., Ltd.), and the mixture was dispersed over a period of 24 hours by means of a ball mill to thereby prepare a dispersed liquid. To this dispersed liquid, with stirring, were added the following components in the order described below, thereby preparing a coating liquid.

Component-1:
13 ml of a silver iodide emulsion (cubic crystal emulsion which contains 20 g of polyvinyl butyral and 0.38 mole of silver per kg of emulsion and average crystal size is 0.03 micron)

Component-2:
3.8 ml of a sensitizing dye (0.05% by weight methanol solution of a merocyanine dye having the following formula:)

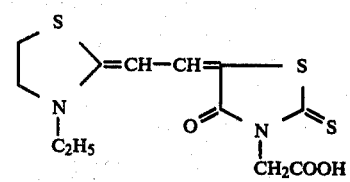

Component-3:
50 ml of ascorbic acid monopalmitate (20% ethanol solution)

Component-4:
40 ml of phthalic acid (10% methanol solution)

Component-5:
15 ml of phthalazine (20% methanol solution)

Component-6:
10 ml of 4-aryl-3-propionamido-5-mercapto-1,2,4-triazole (Compound-3)(2% methanol solution)

The thus obtained coating liquid was coated on a photographic paper support so that the quantity of silver per m² is 0.5 g, whereby a recording material-33 was produced.

And a recording material-34 was prepared in quite the same manner except that in place of the above Component-6, 11.5 ml of a 2% methanol solution of 4-aryl-3-benzoylamino-5-mercapto-1,2,4-triazole (Compound-9) were used, a recording material-35 was prepared likewise by use of 13.0 ml of a 2% methanol solution of 4-aryl-3-p-nitrobenzoylamino-5-mercapto-1,2,4-triazole (Compound-10), a recording material-36 was prepared likewise by use of 11.5 ml of a 2% methanol solution of 4-aryl-3-methanesulfonamido-5-mercapto-1,2,4-triazole (Compound-16), and a recording material-37 was prepared likewise by use of 10 ml of a 2% methanol solution of 2-p-nitrobenzoylamino-5-mercapto-1,3,4-thiadiazole (Compound-24).

For comparison, a recording material-38 was prepared in the identical manner except that in place of Component-6, 9.5 ml of a 2% methanol solution of 4-aryl-3-mercapto-1,2,4-triazole, and a recording material-39 was prepared likewise by use of 8 ml of a 2% methanol solution of 2-mercapto-5-amino-1,3,4-thiadiazole, and further a recording material-40 was prepared in the identical manner except that no compound corresponding to Component-6.

Each of the thus obtained recording materials-33 to -40 was exposed through a step wedge to a white light in the quantity of light of 160 CMS, and then heated to be developed at 120° C. for 10 seconds. The obtained results are as shown in Table 5.

TABLE 5

| Sample No. | Additive compound | Maximum density | Minimum density | Speed (Note 3) |
|---|---|---|---|---|
| 33 | Compound-3 | 1.27 | 0.04 | 425 |
| 34 | Compound-9 | 1.32 | 0.03 | 450 |
| 35 | Compound-10 | 1.30 | 0.03 | 392 |
| 36 | Compound-16 | 1.21 | 0.04 | 368 |
| 37 | Compound-24 | 1.26 | 0.04 | 384 |
| 38 | 4-aryl-3-mercapto-1,2,4-triazole | 0.25 | 0.04 | 62 |
| 39 | 2-mercapto-5-amino-1,3,4-thiadiazole | 0.42 | 0.06 | 146 |

TABLE 5-continued

| Sample No. | Additive compound | Maximum density | Minimum density | Speed (Note 3) |
|---|---|---|---|---|
| 40 | None | 0.30 | 0.05 | 100 |

(Note 3):
The speed values shown in the table are relative values to the speed regarded as 100 of the comparative recording material-40.

EXAMPLE 6

To 22.2 g of silver behenate were added 420 ml of ethanol and 20 g of polyvinyl butyral (Eslec BL-1, produced by Sekisui Chemical Co., Ltd.), and the mixture was dispersed over a period of 24 hours by means of a ball mill, thereby producing a dispersed liquid. To this dispersed liquid, with stirring, were added the following components in the order described below, thus producing a coating liquid.

Component-1:
  13 ml of a silver iodide emulsion (cubic crystal emulsion which contains 20 g of polyvinyl butyral and 0.38 mole of silver per kg of emulsion and average crystal size is 0.03 micron)

Component-2:
  3.8 ml of a sensitizing dye (0.05% by weight methanol solution of a merocyanine dye having the following formula:)

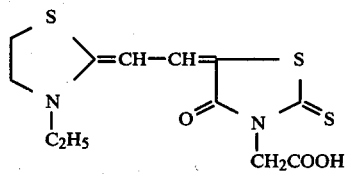

Component-3:
  50 ml of ascorbic acid monopalmitate (20% ethanol solution)

Component-4:
  40 ml of phthalic acid (10% methanol solution)

Component-5:
  15 ml of phthalazine (20% methanol solution)

Component-6:
  10 ml of 4-aryl-3-propionamido-5-mercapto-1,2,4-triazole (Compound-3)(2% methanol solution)

The thus prepared coating liquid was coated on a photographic paper support so that the quantity of silver per m² is 0.48 g, thereby preparing a recording material-41.

And a recording material-42 was prepared in quite the same manner except that in place of the above Component-6, 11.5 ml of a 2% methanol solution of 4-aryl-3-benzoylamino-5-mercapto-1,2,4-triazole (Compound-9), a recording material-43 was prepared likewise by use of 13.0 ml of a 2% methanol solution of 4-aryl-3-p-nitrobenzoylamino-5-mercapto-1,2,4-triazole (Compound-10), a recording material-44 was prepared likewise by use of 11.5 ml of a 2% methanol solution of 4-aryl-3-methanesulfonamido-5-mercapto-1,2,4-triazole (Compound-16), and a recording material-45 was prepared likewise by use of 10 ml of a 2% methanol solution of 2-p-nitrobenzoylamino-5-mercapto-1,3,4-thiadiazole (Compound-24).

For comparison, a recording material-46 was prepared in the identical manner except that in place of the above Component-6, 9.5 ml of a 2% methanol solution of 4-aryl-3-mercapto-1,2,4-triazole, and a recording material-47 was prepared in like manner by use of 8 ml of a 2% methanol solution of 2-mercapto-5-amino-1,3,4-thiadiazole, and further, a recording material-48 was prepared in the identical manner except that no compound corresponding to Component-6 was used.

Each of the thus prepared recording materials-41 to -48 was exposed through a step wedge to a white light in the quantity of light of 160 CMS, and then heated to be developed at 100° C. for 10 seconds. The obtained results are as shown in Table 6.

TABLE 6

| Sample No. | Additive compound | Maximum density | Minimum density | Speed (Note 4) |
|---|---|---|---|---|
| 41 | Compound-3 | 1.32 | 0.21 | 248 |
| 42 | Compound-9 | 1.28 | 0.23 | 254 |
| 43 | Compound-10 | 1.29 | 0.22 | 222 |
| 44 | Compound-16 | 1.20 | 0.20 | 242 |
| 45 | Compound-24 | 1.24 | 0.21 | 204 |
| 46 | 4-aryl-3-mercapto-1,2,4-triazole | 0.62 | 0.22 | 64 |
| 47 | 2-mercapto-5-amino-1,3,4-thiadiazole | 0.89 | 0.26 | 105 |
| 48 | None | 0.80 | 0.24 | 100 |

(Note 4):
The speed values shown in the table are relative values to the speed regarded as 100 of the comparative recording material-48.

As apparent from the results shown in Tables 1-6, in all Examples 1-6, the maximum densities of the samples for the present invention are higher than those of the comparative samples, and in Examples 3-6, the speeds of the samples for the invention are also higher than those of the comparative samples.

What we claim is:

1. A heat-development-type image recording material comprising on a support a heat-development-type image recording layer containing
   (a) an organic silver salt,
   (b) a reducing agent,
   (c) a binder, and
   (d) at least one compound of following formula [I]:

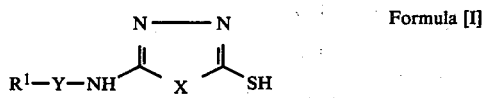

Formula [I]

wherein $R^1$ represents a hydrogen atom, a hydroxy radical or a substituted or unsubstituted alkyl, alkenyl, aryl or alkoxy radical; Y represents a sulfonyl or a carbonyl radical; and X represents a sulfur atom or $=N-R^2$ wherein $R^2$ is a hydrogen atom, an amino radical or a substituted or unsubstituted alkyl, aryl or alkenyl radical.

2. A heat-development-type image recording material according to claim 1 wherein the image recording material contains a light-sensitive silver halide.

3. A heat-development-type image recording material according to claim 1 wherein the image recording material contains a compound of following formula [II]:

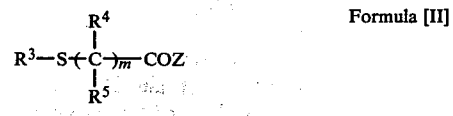

Formula [II]

wherein $R^3$ represents a substituted or unsubstituted alkyl, aryl or heterocyclic radical; $R^4$ and $R^5$ each represents a hydrogen, a substituted or unsubstituted alkyl, aryl or heterocyclic radical; Z represents a hydroxyl or an amino radical; and m is an integer of 1 or 2.

4. A heat-development-type image recording material according to claim 1 wherein the compound of Formula [I] is incorporated in the layer in a quantity of from 0.001 to 10 moles per mole of the organic silver salt.

5. A heat-development-type image recording material according to claim 1 wherein the organic silver salt is a silver salt of an organic compound having an imino radical.

6. A heat-development-type image recording material according to claim 1 wherein the organic silver salt is a silver salt of benzotriazole.

7. A heat-development-type image recording material according to claim 1 wherein the organic silver salt is incorporated in the layer in a quantity of from 0.5 to 50 mg in silver equivalent per dm$^2$ of the layer.

8. A heat-development-type image recording material according to claim 3 wherein the compound of Formula [II] is incorporated in the layer from 0.001 to 10 moles per mole of the organic silver salt.

9. A heat-development-type image recording material according to claim 1 wherein the reducing agent is incorporated in the layer in a quantity of from 0.05 to 10 moles per mole of the organic silver salt.

10. A heat-development-type image recording material according to claim 2 wherein the light-sensitive silver halide is incorporated in the layer in a quantity of from 0.001 to 1.0 mole per mole of the organic silver salt.

* * * * *